(12) United States Patent
Tasker et al.

(10) Patent No.: US 8,047,984 B2
(45) Date of Patent: Nov. 1, 2011

(54) SEXUAL STIMULATION DEVICE

(75) Inventors: Sean J. Tasker, Manchester (GB); Mark V. Critchley, Manchester (GB); Suren Solanki, Cambridge (GB); John D. Joyce, Rubi (ES)

(73) Assignee: LRC Products Limited, Slough, Berkshire (GB)

( * ) Notice: Subject to any disclaimer, the term of this patent is extended or adjusted under 35 U.S.C. 154(b) by 21 days.

(21) Appl. No.: 12/309,037

(22) PCT Filed: Jul. 5, 2007

(86) PCT No.: PCT/GB2007/002530
§ 371 (c)(1),
(2), (4) Date: Jun. 23, 2009

(87) PCT Pub. No.: WO2008/003980
PCT Pub. Date: Jan. 10, 2008

(65) Prior Publication Data
US 2009/0306468 A1    Dec. 10, 2009

(30) Foreign Application Priority Data

Jul. 6, 2006  (GB) .................................. 0613456.3
Dec. 13, 2006  (GB) .................................. 0624872.8

(51) Int. Cl.
*A61F 5/00*        (2006.01)
(52) U.S. Cl. ........................................................ 600/38
(58) Field of Classification Search .............. 600/38–41; 601/72, 80
See application file for complete search history.

(56) References Cited

U.S. PATENT DOCUMENTS

| | | | | |
|---|---|---|---|---|
| 3,941,618 | A  * | 3/1976 | Mabuchi | 429/99 |
| 6,924,966 | B2 * | 8/2005 | Prophet | 361/207 |
| 6,991,600 | B1 * | 1/2006 | Wang | 600/38 |
| 7,341,566 | B2 * | 3/2008 | Nan | 601/72 |
| 2003/0083598 | A1 | 5/2003 | Kobayashi et al. | |
| 2003/0181784 | A1 | 9/2003 | Klein | |
| 2005/0081863 | A1 | 4/2005 | Lin | |
| 2005/0288611 | A1 | 12/2005 | Fang | |
| 2006/0069329 | A1 | 3/2006 | Nan | |
| 2007/0038019 | A1* | 2/2007 | Weng | 600/38 |
| 2008/0077058 | A1* | 3/2008 | Klearman | 601/70 |
| 2009/0012355 | A1* | 1/2009 | Lin | 600/41 |

FOREIGN PATENT DOCUMENTS

| DE | 20311823 | 9/2003 |
|---|---|---|
| GB | 2413496 | 11/2005 |

OTHER PUBLICATIONS

English Abstract of DE20311823.

* cited by examiner

*Primary Examiner* — Samuel Gilbert
(74) *Attorney, Agent, or Firm* — Ryan A. Schneider; Troutman Sanders LLP

(57) ABSTRACT

A sexual stimulation device (1) includes a casing (2) with a vibrator unit disposed therein, the vibrator unit including an electric motor with an eccentric mass mounted on its output shaft. A connection loop (5) is integrally attached to the casing for connecting the device to the penis. A resiliently depressible button (3) is provided for switching the device on and off. A switch of the vibrator unit is bi stable so that the device is turned on and off by pressing the button (3) in the same direction.

17 Claims, 5 Drawing Sheets

SEXUAL STIMULATION DEVICE

The present invention relates to sexual stimulation devices.

In the prior art various sexual stimulation devices are known. For example, so-called electric condom rings comprise an elastic ring for fitting over the penis, with an electric vibrating device connected to the ring. A switch is provided to turn on and off the vibrating device.

GB2414938 discloses an electric condom ring wherein the on/off switch comprises a push rod, which when pushed in, moves an insulation plate to effect an electrical connection between a battery and an electric motor. An eccentric mass is connected to the electric motor for producing vibrations when the motor rotates. The push rod has been known to be accidentally pushed in while the product is in storage or transit, and once this has occurred, there is little chance of the push rod accidentally being pulled outwardly so as to turn off the device. Consequently, when the electric condom ring comes to be used, its battery is flat and the condom ring is thus to be discarded. The push rod is also rather small and so is fiddly to operate.

The present invention provides a sexual stimulation device comprising a casing having a vibrator unit disposed therein, the vibrator unit comprising a housing in which is disposed an electric motor provided with a rotatably driveable eccentric mass whereby operation of the electric motor produces vibrations, a battery being disposed in the housing for providing power to the electric motor, an electrical conductor connecting a pole of the battery to a first electrode of the electric motor and a switch connecting the other pole of the battery to a second electrode of the electric motor wherein the switch comprises a bi stable actuating means pushable in one direction to switch on the electric motor and pushable in the same direction to switch off the electric motor, and the housing comprises a resiliently depressible sealing element surmounting the actuating means.

It is advantageously particularly simple to operate the switch, as the user merely has to press the actuating means to turn the device on, and press again to turn the device off. The actuating means can advantageously be positioned on the device so as to avoid accidental switching on of the device. By virtue of the actuating means turning the vibrator unit on and off by pressing in the same direction, it is advantageously provided that if the device is accidentally switched on it is more likely than the prior art devices to be accidentally switched off again.

By virtue of disposing the vibrator unit in the casing, the vibrator unit is protected from fluids thereby helping to prevent short circuiting within the vibrator unit, and the device is thus also hygienic. Further protection from fluids is afforded by virtue of the housing comprising a resiliently depressible sealing element which surmounts the actuating means.

The sealing element can comprise a relatively soft and compressible material compared to the other components of the device. This can advantageously allow the casing, which abuts the periphery of the sealing element effectively to dig in to the sealing element and form a particularly effective seal therewith.

The vibrator unit comprises a housing which may comprise a pair of half shells which can be sealed together, further contributing to the watertightness of the device. In a preferred embodiment, the half shells are sealed together using ultrasonic welding, which gives a particularly good sealing of the housing and is a convenient mode of manufacture.

Water resistance test have been carried out on embodiments of the invention, in particular against the requirements of European Standard BS EN 60529:1992 (Degrees of protection provided by enclosures). A first test (IP code IPX6) measured the resistance of the device according to the invention and the vibrator unit according to the invention against ingress of water under conditions of powerful jetting, while a second text (IP code IPX7) measured resistance against water under conditions of temporary immersion. Both the device and the vibrator unit passed both tests.

Several prior art devices were also tested against these standards. In one such type of prior art device, the on-off switch takes the form of a sliding switch, while in another type the device is switched on by removing a non-replaceable small plastic strip. In this latter type of device, once switched on, the device cannot be turned off and it vibrates until the batteries run out of energy. All of these prior art devices failed the above waterproofness test.

As referred to above, the fact that the device and vibrator unit according to the invention have a good level of waterproofing protects the electronic equipment situated inside the vibrator unit from the potentially harmful effects of liquids, such as short-circuiting and corrosion of metallic components. Fluids emanating from the user(s) are also prevented from infiltrating the device and the vibrator unit, whereby the invention is hygienic. If such fluids were allowed to linger within the device, bacteria could build up, making the device potentially harmful.

Advantageously the actuating means of the switch can be situated towards a side of the vibrator unit which in use is distal from the penis whereby the actuating means is unlikely to be accidentally knocked during use. This helps to prevent inadvertent turning on or off of the device during use.

The present invention also provides a vibrator unit for a sexual stimulation device comprising a housing in which is disposed an electric motor provided with a rotatably driveable eccentric mass whereby operation of the electric motor produces vibrations, a battery being disposed in the housing for providing power to the electric motor, an electrical conductor connecting a pole of the battery to a first electrode of the electric motor and a switch connecting the other pole of the battery to a second electrode of the electric motor wherein the switch comprises a bi stable actuating means pushable in one direction to switch on the electric motor and pushable in the same direction to switch off the electric motor, and the housing comprises a resiliently depressible sealing element surmounting the actuating means. The vibrator unit thereby has an advantageously simple way of switching on and off, by virtue of which, the vibrator unit can be used in many different devices, with a minimum of adaptation of the device or the vibrator unit being necessary. Further, as discussed above, the vibrator unit has a good level of watertightness.

There now follows a detailed description of an embodiment of the invention by way of example with reference to the accompanying drawings, in which FIG. 1 shows in perspective a sexual stimulation device according to the invention;

FIG. 7 shows the contents of the vibrator unit with the switch turned on;

Figure 1:
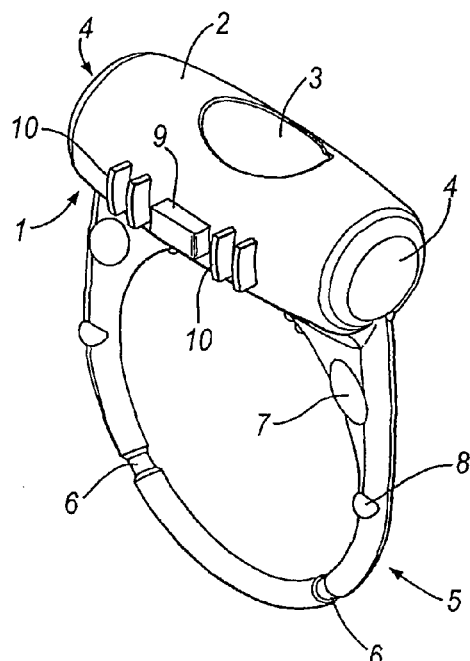

The sexual stimulation device 1 illustrated in FIGS. 1 to 4 comprises a casing 2 made of a flexible rubber material, defining a resilient sleeve. A vibrator unit is located inside the casing 2. On top of the casing, directly opposite the side of the casing which in use faces the penis is an on/off push button 3. The button 3 is lozenge-shaped and comprises a resiliently compressible sealing element, which may optionally be sealed to the vibrator unit within the casing 2, so as to be waterproof. Alternatively, the seal may be water resistant. The casing 2 defines a hole through which the button 3 protrudes, though not necessarily all the way through the hole. Thus, the casing covers all of the vibrator unit apart from the button 3 of the vibrator unit. In manufacture, the vibrator unit is inserted into the casing through the hole. As an alternative, the casing 2 and the button 3 could be integral whereby a watertight seal would be guaranteed. This would require a different method of disposing the vibrator unit in the casing 2, e.g. moulding the casing around the vibrator unit. The vibrator unit 40 is inserted into the casing as a pre-assembled unit and by virtue of its easily operable switching mechanism is usable in many different types of device with a minimum of adaptation of the device or the vibrator unit being necessary. The primary considerations in this respect are that the device is configured to allow the push button 3 to be pressed, and has sufficient space to accommodate the vibrator unit.

The casing has two closed end regions 4, each of which has the shape of a truncated dome, with a substantially flat, circular end face. On a front face of the casing there is provided a protuberance, in particular a raised nodule 9 for stimulating the clitoris, which nodule 9 can be of cuboidal shape. On each side of the nodule 9 there is provided a pair of raised ridges 10 which may serve a similar purpose.

Connected to the casing 2 and preferably integral therewith are connection means 5 for attaching the device to the penis. Provided on a front face of the connection means 5 are a number of protrusions 7, 8 which may further serve to stimulate the vagina. The connection means 5 defines a resilient ring or loop which can be made of any suitable elastic rubber material, and includes at least one weak point which in the embodiment shown comprises a pair of constrictions 6 in the material of the resilient loop 5. The purpose of the weak points 6 is to allow easy and fast removal of the device (by breaking the resilient loop) should this be necessary.

Figure 2:
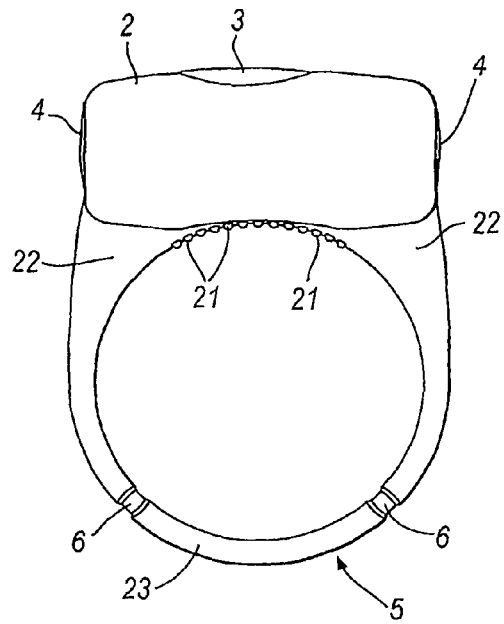
FIG. 2 is a rear elevation of the device of FIG. 1.
Figure 3:
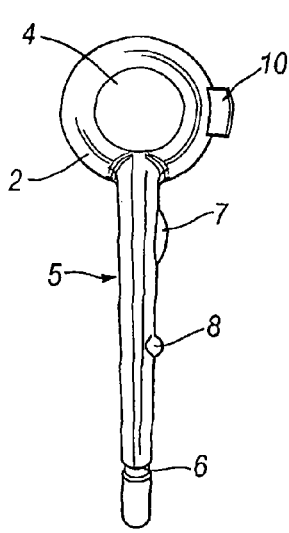
FIG. 3 is a side elevation of the device of FIG. 1.
Figure 4:
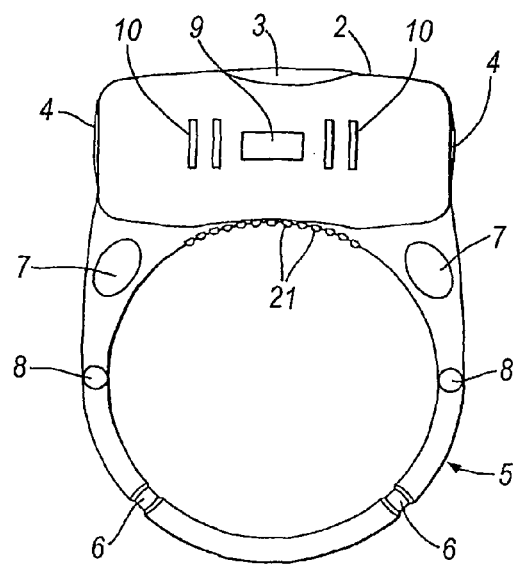
FIG. 4 is a front elevation of the device of FIG. 1.

As best seen in FIG. 2, which shows the rear face of the device, the connection means 5 comprise a region 22 proximal to the casing 2 which is broader in cross-section than a region 23 of the connection means distal to the casing. In other words, the connection means 5 taper away from the casing. This provides a strong connection between the casing 2 and the connection means 5, whilst allowing other regions of the connection means 5 to stretch easily. On the inner periphery of the connection means 5 there are provided a series of small bumps or ridges 21 which facilitate the holding of the device in place on the penis. In particular, the bumps 21 are located by the casing 2.

As may be seen in FIG. 2, the diameter of the resilient loop 5 is approximately the same as the length of the casing 2. Further, the end faces 4 of the casing 2 are continuous with the resilient loop, again providing a strong connection between the resilient loop 5 and the casing 2 as well as an aesthetically appealing design. Preferably the casing 2 and the connection means 5 are an integral component, in particular moulded in one piece, but they may be formed separately and then connected together. The vibrator unit 40 is oriented within the casing 2 generally tangentially with respect to the resilient loop 5.

Figure 5:
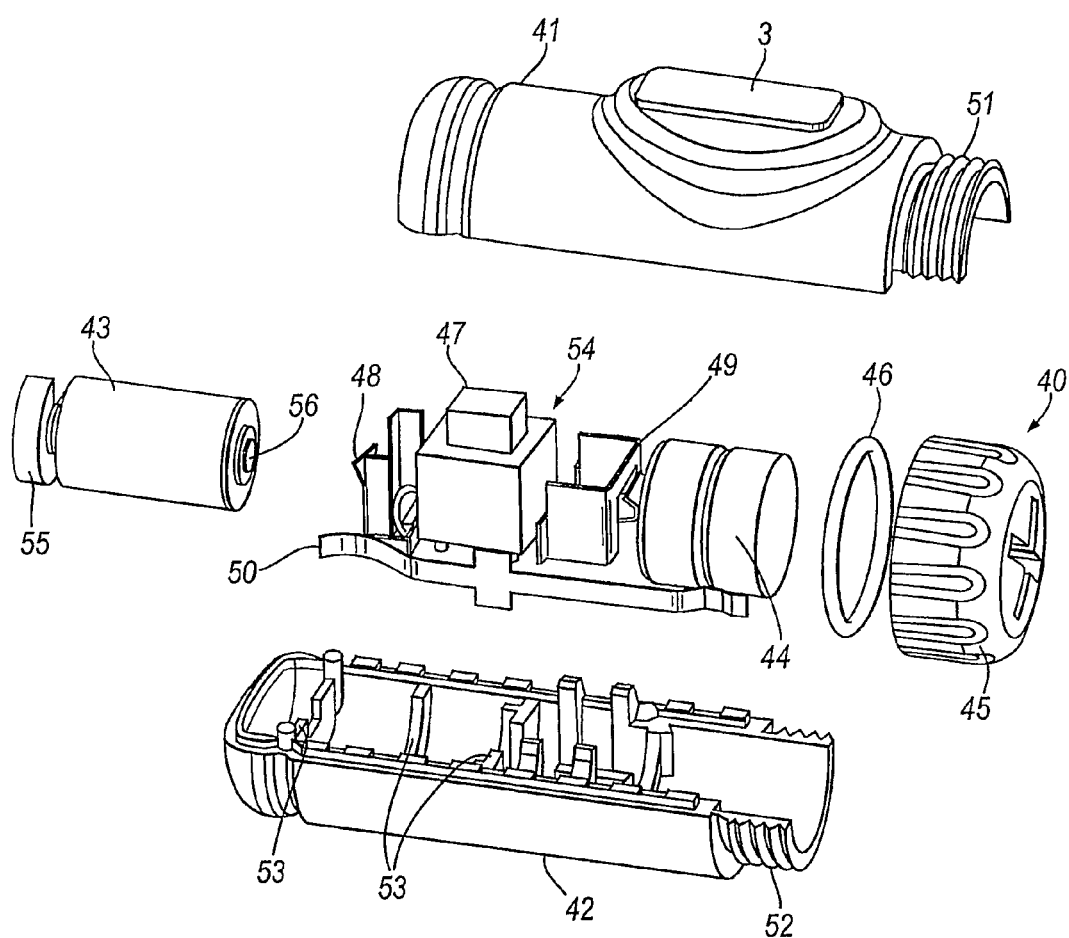
FIG. 5 is an exploded view of a vibrator unit used in the device shown in FIG. 1.

The vibrator unit 40 which is illustrated in exploded form in FIG. 5, comprises a housing assembled from first and second generally semi-cylindrical half shells 41 and 42 which may be manufactured by moulding. At least one of the half shells 41, 42 includes internal ribs 53 which serve to hold the contents of the housing in place. The half shells 41, 42 include respective threaded portions 51, 52 at an end thereof arranged such that when the half shells 41, 42 are brought together the threaded portions 51, 52 define a threaded tubular connector to which an end-cap, e.g. a screw-cap 45 is attachable and may serve to hold the shells 41, 42 together. Alternatively, or additionally, the housing half shells 41, 42 may snap-fit together. On top of the first half shell 41, the operating button 3 is located.

The components accommodated inside the housing 41, 42 are an electric motor 43, a switch 54 and one or more batteries 44 (in the present embodiment, two batteries), as well as various electrical contacts. The electric motor has an eccentric mass 55 connected to its output drive shaft whereby operation of the electric motor produces vibrations. An electrical conductor 50 comprising an elongate metallic strip connects a first electrode of the electric motor, the first electrode comprising a side of a metallic housing of the motor 43, to a pole of the battery 44 formed by a side of a metallic casing of the battery. Situated in a cavity defined between the electric motor and the battery is a switch 54 for switching the electric motor 43 on and off. The switch may be partially located in the cavity or can be entirely within the cavity. The switch 54 includes bi-stable actuating means 47 comprising a push-button 47 which is depressed by the user to operate the switch to turn on the electric motor 43. To switch off the electric motor 43, the user depresses the push-button 47 again. In practice, of course, the user depresses the resilient rubber button 3 on the vibrator unit housing, which is situated directly adjacent to the push-button 47. On either side of the switch 54, there are provided first and second contact means 48, 49 comprising first and second metallic contact plates. The first metallic plate 48 establishes an electrical connection between a pole 56 of the electric motor situated on a longitudinal end face of the electric motor, and a first terminal 61 of the switch (see FIG. 5), whereas the second metallic contact plate 49 establishes an electrical connection between a pole of the battery 44 defined by an end face of the battery 44 and a second terminal 62 of the switch 54. The primary purpose of the metallic plates 48, 49 is to adapt the switch 54 which is a standardised component, to the particular application in hand. The metallic plates 48, 49 may include contacting portions which are resiliently biased against the components with which they are in contact to provide a good electrical connection. An O-ring 46 is disposed around the threaded tubular connector formed by the two housing shells 41, 42, serving to seal the connection between the housing and the screw-cap 45. An annular groove extends around the housing adjacent the end opposite the cap 45 and may receive a rib moulded on the inside of the casing easing to assist location of the vibrator unit within the outer casing.

Figure 6:
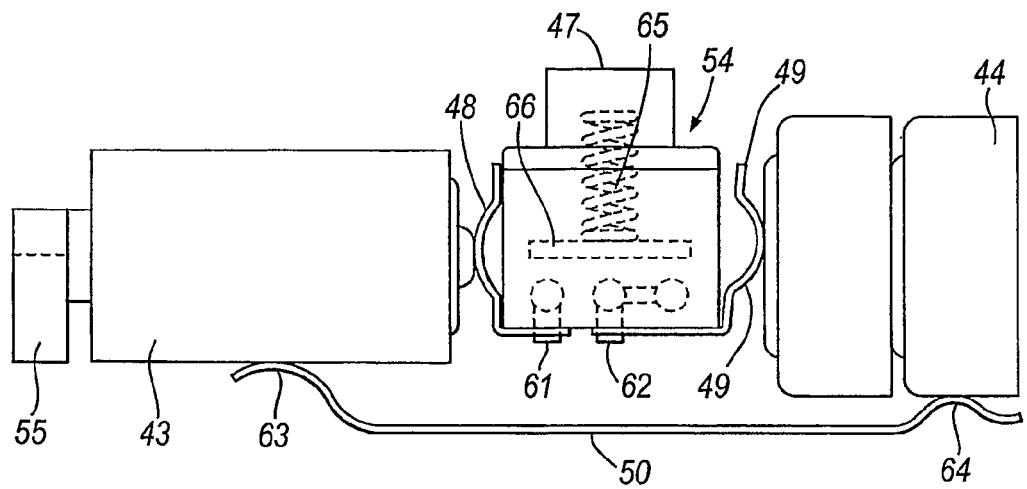
FIG. 6 shows the contents of the vibrator unit with a switch turned off.
Figure 7:
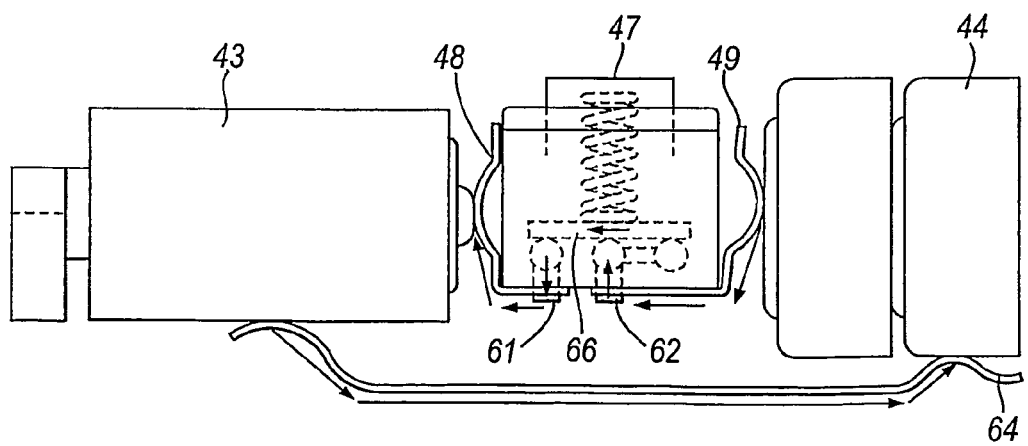

The inner working components of the vibrator unit are shown assembled together in FIGS. 6 and 7, with the switch 54 being in the "off" state in FIG. 6 and in the "on" state in FIG. 7. The actuating button 47 of the switch 54 is connected by a spring 65 to an electrically conductive switch plate 66 which is movable to a position bridging a gap between two contact terminals 61 and 62, illustrated in FIG. 7, thereby completing the circuit for switching on the electric motor.

Inside the switch are latching means for making the actuating button 47 bi-stable, so that the switch remains in the on condition until the actuating button is depressed again so that the switch contact plate 66 returns to the "off" position of FIG. 6. The electrical conductor 50 has a first curved portion for contacting the side of the electric motor 43 and a second curved portion 64 for contacting the side of the battery 44.

Figure 8:
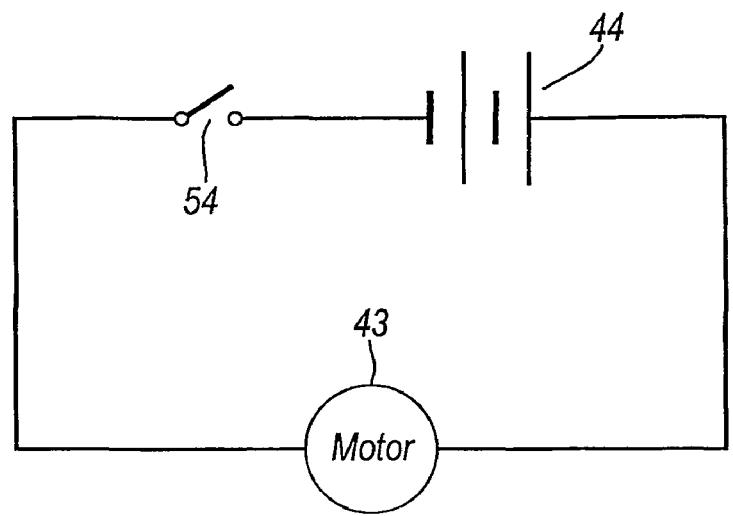
FIG. 8 shows a simplified schematic circuit diagram of the vibrator unit.

FIG. 8 is a simple circuit diagram showing schematically the electrical connections between the switch 54, the battery 44 and the electric motor 43. In the present embodiment the two batteries 44 are connected in series, but it would also be possible to connect the batteries in parallel with one another to produce vibrations of a lower power. In this regard, the internal components of the vibrator unit can be arranged to allow the user to choose between a series connection or a parallel connection of the batteries, e.g. by pressing the push button 3.

Figure 9:
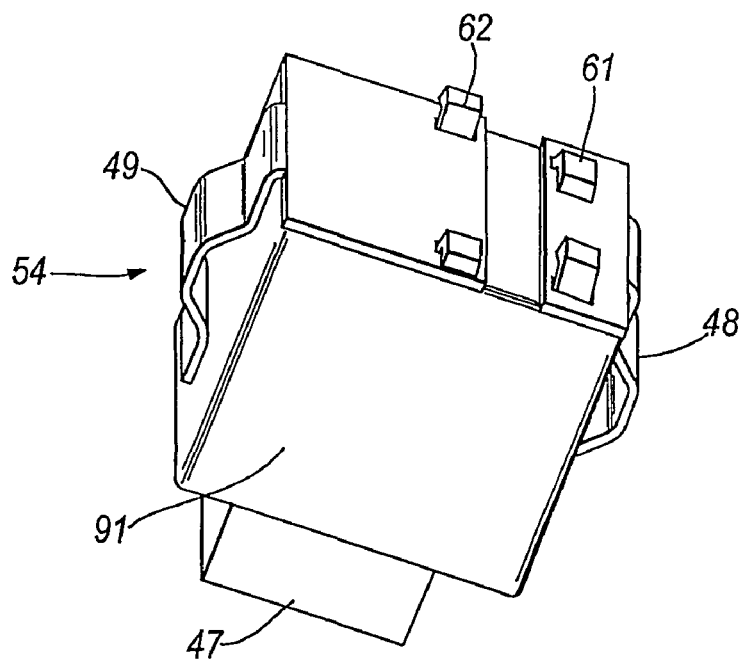
FIG. 9 shows in perspective the switch used in the vibrator unit.

FIG. 9 shows a detail of the switch 54, including the first and second contact plates 48, 49 (in a slightly different configuration to that shown in FIG. 5), the electrical terminals 61, 62 and the actuating means 47. The housing 91 of the switch is made from plastics material whereas the contact plates 48, 49 and terminals are metallic.

Figure 10:
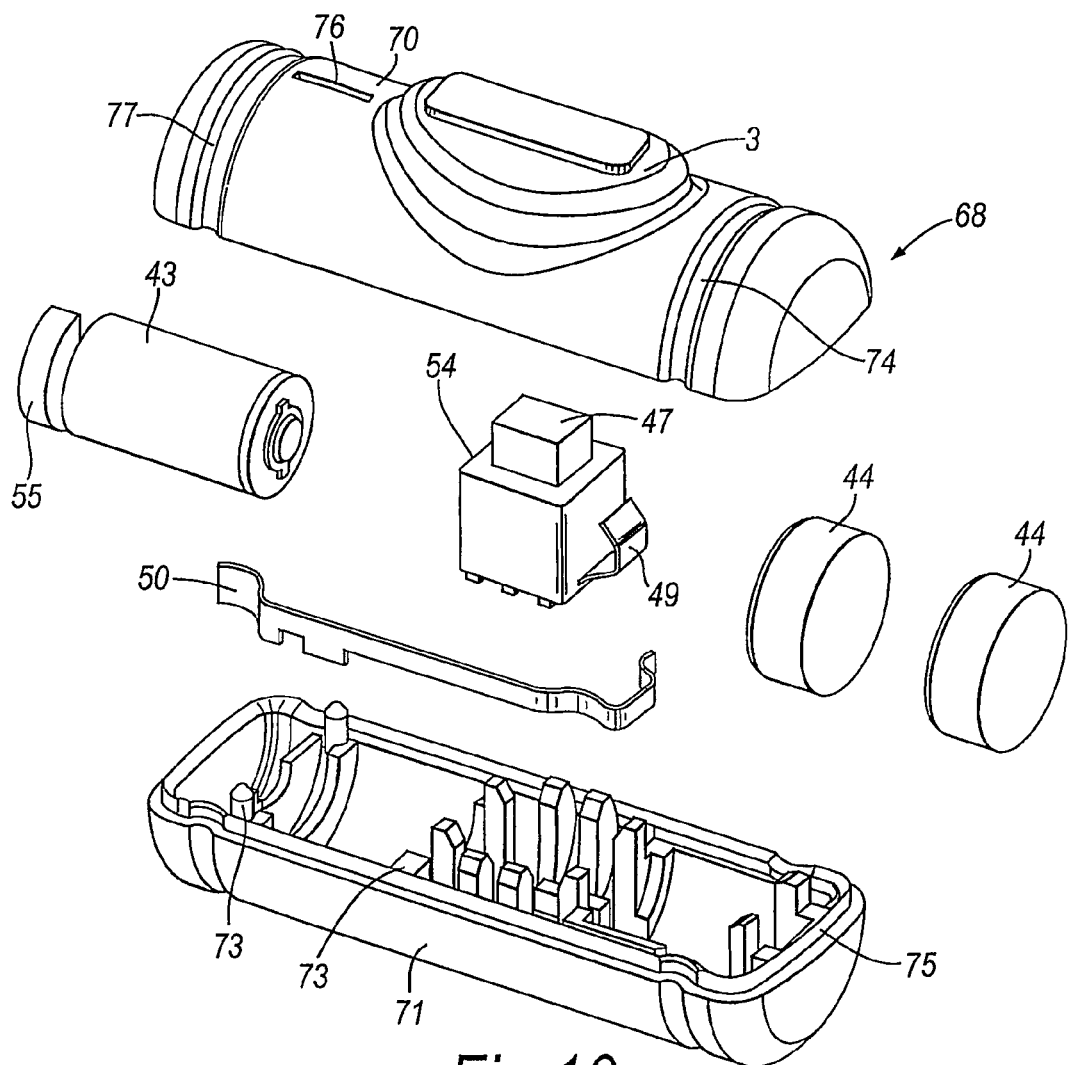
FIG. 10 is an exploded view of a second embodiment of vibrator unit for use in the device of FIG. 1.
Figure 11:
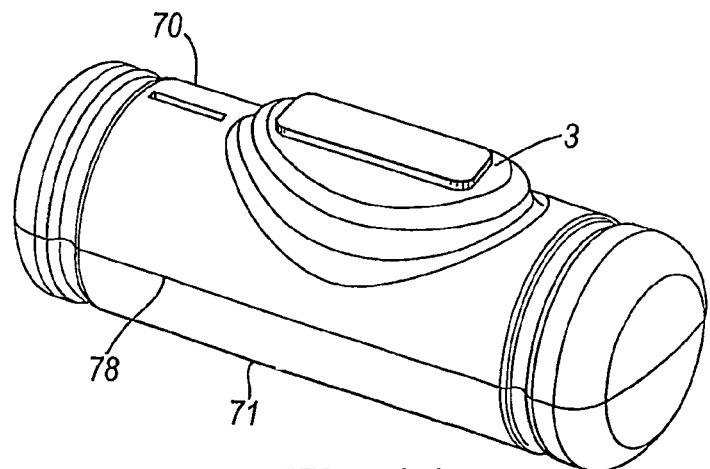
FIG. 11 is a perspective view of the vibrator unit of FIG. 10 in assembled form.

FIG. 10 shows an alternative, preferred embodiment of the vibrator unit 68 which is generally similar to the vibrator unit shown in FIG. 5, and like reference numerals are used to represent like components thereof. The main difference is that the first and second generally semi-cylindrical half shells 70, 71 are to be connected to each other by sealing or in other words non-mechanically. This leads to a good waterproofing of the vibrator unit, which may exceed the level of waterproofing provided when the half-shells are connected together mechanically. Advantageously, the sealing can be effected continuously around the perimeter edges of the half-shells 70, 71 along which the half-shells engage one another, and in particular around the entire perimeter. Various methods of sealing may be employed, including for example welding (e.g. ultra-sonic welding and/or rf welding), or chemical sealing, and adhesives may be used. The sealing thus effected is permanent, in that separation of the half-shells 70, 71 destroys the seal. The currently preferred method of sealing is ultra-sonic welding. In the embodiment of the vibrator unit shown in FIG. 5 the end cap 45 is provided for closing the housing and helping to hold the shells 41, 42 together. The end cap 45 is removable, allowing replacement of the batteries 44. In the embodiment of FIG. 10, it is not possible for the user to detach the half-shells 70, 71 from one another and then to re-attach them, and thus the vibrator unit 68 is intended to be disposable when the batteries 44 run out. This disposability leads to improved hygiene because it is not possible to re-use the device over a time period longer than the battery life. One of the half-shells 71 includes a flange 75 extending around its perimeter, and a corresponding rebate is provided along the perimeter of the other half-shell 70 for receiving the flange. This structure provides a larger surface area of connection between the shells than otherwise would be present, and thus helps the sealing process to fuse the two half-shells 70, 71 together strongly.

In the embodiment of the vibrator unit of both FIGS. 5 and 10, the push button 3 comprises a resilient material which is soft and compressible compared to the material from which the shells 40, 41, 70, 71 are manufactured. One particular way of producing this bi-material shell is to use a two-shot moulding process, wherein a first material is injected into the mould to create one part of the shell and a second material is then injected to create the other part of the shell. This also allows different colours to be used for the parts of the shell. It is of course also possible to make the parts separately and then connect them together.

The vibrator unit 68 includes a pair of annular grooves 74, 77, in distinction to the single groove provided on the housing of the first embodiment of the vibrator unit. An extra rib can be moulded on the inside of the casing corresponding to the additional groove, and this helps to ensure that the vibrator unit is positioned correctly within the casing when it is inserted during manufacture.

A small indent 76 is provided on one of the half shells 70, 71, which is used to assist with aligning the vibrator unit when it is being inserted into the casing. Instead of the indent 76, a mark or a slit may optionally be used.

The metallic contact plates 48, 49 adjacent to the switch 54, as shown in FIG. 5, are dispensed with in the embodiment shown in FIG. 10, and the switch 54 is as shown in FIG. 9, including contact plates 48, 49, smaller than those of FIG. 5. The resulting structure is simple and therefore the unit 68 is easy to manufacture.

The nominal life of the batteries 44 is chosen to be approximately 20 minutes. The reason for this is that there is a risk of damage to the penis if the device is used or worn for too long. A limit of 30 minutes per use has been proposed. In the embodiment shown, two G3-A 1.5V batteries with a 35 mAh capacity are used.

This provides a current of approximately 100 mA and a nominal battery life of 21 minutes. The overall energy provided by the batteries is 3V multiplied by 35 mAh, or 105 mWh. This represents an increase in total energy over some prior vibrator units, which may have a longer life than the current device but produce vibrations of a significantly lower power. In comparative tests of the vibrator unit, an accelerometer was used to measure the strength of the vibrations produced, relative to prior devices. The vibrator units disclosed herein produced a measured acceleration of up to 6 g (where g is the acceleration due to gravity) which was considerably higher than the prior vibrator units were able to produce.

Although FIGS. 5 and 10 show the vibrator unit comprising longitudinal half-shells, i.e. shells which define a plane of connection along the length of the unit, other configurations would be possible. For example, the vibrator unit may comprise a cylinder with an end cap at one or both ends which can be screwed or sealed thereon. Alternatively, the half-shells could define a plane of connection which is perpendicular to the length of the vibrator unit and which may bi-sect the vibrator unit. An obliquely angled plane of connection would also be possible.

The invention claimed is:

1. A sexual stimulation device comprising a casing having a vibrator unit disposed therein, the vibrator unit comprising a housing in which is disposed an electric motor provided with a rotatably drivable eccentric mass whereby operation of the electric motor produces vibrations, a battery in the housing for providing power to the electric motor, an electrical conductor connecting a pole of the battery to a first electrode of the electric motor and a switch connecting the other pole of the battery to a second electrode of the electric motor wherein the switch comprises a bi stable actuating means pushable in one direction to switch on the electric motor and pushable in the same direction to switch off the electric motor, and the housing comprises a resiliently depressible sealing element surmounting the actuating means, and wherein the switch is situated in a cavity defined between the electric motor and the battery.

2. The device according to claim 1, including connection means for connecting the device to a penis.

3. The device according to claim 2, wherein the connection means are connected to and formed in one piece with the casing.

4. The device according to claim 3, wherein the connection means comprise a resilient loop for extending around the penis, the resilient loop having a greater cross-section in a region proximal to the casing than in a region distal to the casing.

5. The device according to claim 4, wherein the connection means comprise a predetermined weak point.

6. The device according to claim 5, wherein the connection means include one or more forwardly-facing protrusions.

7. The device according to claim 6, wherein the actuating means of the switch is situated towards a side of the vibrator unit which in use is distal from the penis.

8. The device according to claim 7, wherein the casing comprises a resilient sleeve into which the vibrator unit is inserted.

9. The device according to claim 8, wherein the ends of the casing are closed whereby the casing encloses the ends of the vibrator unit.

10. The device according to claim 9, wherein the casing defines a hole located adjacent to the actuating means, through which hole the vibrator unit is inserted into the casing.

11. A vibrator unit for a sexual stimulation device comprising a housing in which is disposed an electric motor provided with a rotatably drivable eccentric mass whereby operation of the electric motor produces vibrations, a battery in the housing for providing power to the electric motor, an electrical conductor connecting a pole of the battery to a first electrode of the electric motor and a switch connecting the other pole of the battery to a second electrode of the electric motor wherein the switch comprises a bi stable actuating means pushable in one direction to switch on the electric motor and pushable in the same direction to switch off the electric motor, and the housing comprises a resiliently depressible sealing element surmounting the actuating means, and wherein the housing comprises a pair of generally semi-cylindrical half shells.

12. The vibrator unit according to claim 11, wherein the half shells are sealed together by ultra-sonic welding.

13. The vibrator unit according to claim 12, wherein a groove extends around the housing at an end region thereof.

14. A vibrator unit for a sexual stimulation device comprising:
a housing comprising a resiliently depressible sealing element;
an electric motor disposed in the housing comprising a rotatably driveable eccentric mass, a first electrode, and a second electrode, wherein operation of the electric motor produces vibrations;
a battery in the housing for providing power to the electric motor, the battery having a first pole and a second pole;
an electrical conductor connecting the first pole of the battery to the first electrode of the electric motor; and
a switch connecting the second pole of the battery to the second electrode of the electric motor, the switch comprising a bi stable actuating means pushable in one direction to switch on the electric motor, and pushable in the same direction to switch off the electric motor;
wherein a cavity is defined between the electric motor and the battery;
wherein the resiliently depressible sealing element of the housing surmounts the actuating means; and
wherein the switch is situated in the cavity.

15. The vibrator unit according to claim 14, the housing comprising a pair of generally semi-cylindrical half shells.

16. The vibrator unit according to claim 15, wherein the half shells are sealed together by ultra-sonic welding.

17. The vibrator unit according to claim 16, the housing further comprising a groove extending around the housing at an end region thereof.

* * * * *